US005801027A

United States Patent [19]
Bennett et al.

[11] Patent Number: 5,801,027
[45] Date of Patent: Sep. 1, 1998

[54] METHOD OF USING TRANSACTIVATION PROTEINS TO CONTROL GENE EXPRESSION IN TRANSGENIC PLANTS

[75] Inventors: Malcolm Bennett, Claycroft Hall; Sean May, Earlsdon; Nicola Ramsay, Bishopston, all of England

[73] Assignee: University of Warwick, United Kingdom

[21] Appl. No.: 452,267

[22] Filed: May 26, 1995

[30] Foreign Application Priority Data

Feb. 8, 1995 [GB] United Kingdom .................. 9502456

[51] Int. Cl.$^6$ .................. C12N 15/29; C12N 15/82; A01H 5/00; A01H 4/00
[52] U.S. Cl. .................. 435/172.3; 435/320.1; 435/419; 800/205; 736/24.1; 736/23.74
[58] Field of Search .................. 435/172.3, 240.4, 435/320.1, 419; 800/205; 536/24.1, 23.74

[56] References Cited

U.S. PATENT DOCUMENTS 5,409,823  4/1995  Crossland et al. .................. 435/172.3

FOREIGN PATENT DOCUMENTS

WO92/19747  11/1992  WIPO .

OTHER PUBLICATIONS

University of Warwick, "Farmers could cultivate crops of plastic: New technique opens door to cheap cultivation of plastics in transgenic oilseed rape", Press Release, May 26, 1995.
Koning et al., "Arrest of embryo development in *Brassica napus* mediated by modified *Pseudomonas aeruginosa* exotoxin A", Plant Mol. Biol., vol. 18, pp. 247–258, (1992).
O'Kane et al., "Detection in situ of genomic regulatory elements in Drosophila", PNAS (USA), vol. 84, pp. 9123–9127, (1987).
Johnston, "A Model Fungal Gene Regulatory Mechanism: the GAL Genes of *Saccharomyces cerevisiae*", Microbiol. Rev., vol. 51 (4), pp. 458–476, (1987).
Ma et al., "Deletion Analysis of GAL4 Defines Two Transcriptional Activating Segments", Cell, vol. 48, pp. 847–853, (1987).
Brent et al., "A Eukaryotic Transcriptional Activator Bearing the DNA Specificity of a Prokaryotic Repressor", Cell, vol. 43, pp. 729–736, (1985).
West et al., "Saccharomyces cerecisiae GAL1–GAL10 Divergent Promoter Region: Location and Function of the Upstream Activating Sequence UAS$_G$", Mol. Cell. Biol., vol. 4(11), pp. 2467–2478, (1984).
Giniger et al., "Specific DNA Binding of GAL4, A Positive Regulatory Protein of Yeast", Cell, vol. 40, pp. 767–774, (1985).
Lorch et al., "A Region Flanking the GAL7 Gene and a Binding Site for GAL4 Protein as Upstream Activating Sequences in Yeast", J. Mol. Biol., vol. 186, pp. 821–824, (1985).
Keegan et al., "Separation of DNA Binding from the Transcription–Activating Function of a Eukaryotic Regulatory Protein", Sci., vol. 231, pp. 699–704, (1986).
Johnston et al., "Genetic evidence that zinc is an essential co-factor in the DNA binding domain of GAL4 protein", Nature, vol. 328, pp. 353–355, (1987).
Marmorstein et al., "DNA recognition by GAL4:structure of a protein–DNA complex", Nature, vol. 356, pp. 408–414, (1992).
Carey et al., "An Amino-terminal Fragment of GAL4 Binds BNA as a Dimer", J. Mol. Biol. vol. 209, pp. 423–432, (1989).
Silver et al., "Amino terminus of the yeast GAL4 gene product is sufficient for nuclear localization", PNAS (USA), vol. 81, pp. 5951–5955, (1984).
Lin et al., GAL4 Derivatives Function Alone and Synergistically with Mammalian Activators in Vitro, Cell. vol. 54, pp. 659–664, (1988).
Kakidani et al., "GAL4 Activates Gene Expression in Mammalian Cells", Cell. vol. 52, pp. 161–167, (1988).
Webster et al., "The Yeast UAS$_G$ is a Transcriptional Enhancer in Human HeLa Cells in the Presence of the GAL4 Trans–Activator", Cell, vol. 52, pp. 169–178, (1988).
Ma et al., "Yeast activators stimulate plant gene expression", Nature, vol. 334, pp. 631–633, (1988).
Brand et al., "Targeted gene expression as a means of altering cell fates and generating dominate phenotypes", Development, vol. 118, pp. 401–415, (1993).
Greig et al., "Homeotic genes autonomously specify one aspect of pattern in the Drosophila mesoderm", Nature, vol. 362, pp. 630–632, (1993).
Yanisch–Perron et al., "Improved M13 phage cloning vectors and host strains: nucleotide sequences of the M13mp18 an pUC19 vectors", Gene, vol. 33, pp. 103–119, (1985).
Jefferson et al., "GUS fusions: β–glucuronidase as a sensitive and versatile gene fusion marker in higer plants", EMBO J., vol. 6(13), pp. 3901–3907, (1987).
Odell et al, "Identification of DNA sequences required for activity of the cauliflower mosaic virus 35S promoter", Nature, vol. 313, pp. 810–812, (1985).

(List continued on next page.)

*Primary Examiner*—Douglas W. Robinson
*Assistant Examiner*—Thomas Haas
*Attorney, Agent, or Firm*—Barnes & Thornburg

[57] ABSTRACT

The invention discloses methods of controlling one or more genes in plants. The genes may be exogenous genes and produce a desired phenotypic trait in the plants produced. The genes are operatively linked to a heterologous upstream activating sequence (UAS) recognition site, which is activatable by a transactivating protein, such as GAL4. The genes linked to the UAS sequence, and nucleic acid encoding for the transactivating protein may originally be in separate transgenic plants, one of which fertilises the other to produce reproductive material, such as seed, which may be grown into plants expressing the desired phenotype. The desired phenotype may be herbicide resistance or the production of a polyhydroxyalkanoate, such as polyhydroxybutyrate.

20 Claims, 7 Drawing Sheets

OTHER PUBLICATIONS

Vancanneyt et al., "Construction of an intron-containing marker gene: Splicing of the intron in transgenic plants and its use in monitoring early events in Agrobacterium-mediated plant transformation", Mol.Gen.Gent., vol. 220, pp. 245–250, (1990).

Weinmann et al., "A chimeric transactivator allows tetracyline-responsive gene expression in whole plants", The Plant Journal, vol. 5(4), pp. 559–569 (1994).

Poirier et al., "Polyhydroxybutyrate, a Biodegradable Thermoplastic, Produced in Transgenic Plants", Science, vol. 256, pp. 520–523 (1992).

METHOD OF USING TRANSACTIVATION PROTEINS TO CONTROL GENE EXPRESSION IN TRANSGENIC PLANTS

The current application relates to the control of transgenes in plants by the use of a transactivating protein.

The commercial exploitation of plants using genetic engineering has been an industrial goal for over a decade. Conventional approaches to the regulation of plant transgene expression by the fusing of a highly expressed promoter element directly with the gene coding sequence has proved insufficient to meet the stringent safety and technical demands of plant biotechnology today. Environmentally there is a serious risk of genetically releasing an actively expressed trait, such as herbicide resistance, into plant populations. Commercially the exploitation of plants by transgenic modification, as described for example by Koning et al (Plant Mol. Biol. Vol 18, pages 247–258 (1992)), such as through the introduction of a novel biochemical pathway such as polyhydroxybutyrate synthesis (described in WO92/19747 (ICI)) is hampered by our inability. to introduce and coordinately regulate multiple transgenes in transgenic crops. The conventional approach would involve fusing each biosynthetic gene to a common promoter element, followed by their repeated transformation into a transgenic plant, as described for example in WO92/19747 (ICI). Practically, this approach is time-consuming, limits further alterations of transgene expression and rather than enabling coordinate transgene expression can lead to cosuppression of other transgenes (O'Kane & Gehring, PNAS (USA), Vol. 84, pages 9123–9127. (1987)).

The inventor proposes a novel approach to the control of transgenes in plants. Instead of using the regulatory and expressed sequences in conventional cis fashion, they propose to rearrange them so that they are used in a trans fashion.

The promoter element now indirectly regulates the transgene(s) via a transcriptional activating protein intermediate. The immediate outcome of this is that two plant lines can be produced; one which contains transgene(s) encoding for a desired phenotype and one which contains a transgene encoding for the regulatory transactivating protein. This means that the desired phenotypic trait is only fully expressed once both of the sets of transgenes have come together in an F1 hybrid plant. The regulatory and phenotype transgenes will then segregate apart in subsequent generations.

This has major safety implications because it means that the chances of an active transgene encoding for a phenotypic trait, such as herbicide resistance, being released into the environment is considerably reduced. Safety can be further enhanced by making one of the plants containing the transgenes male sterile, so that pollen contain the transgene is not released. This also has advantages for seed companies marketing high value genetically engineered traits because, if a farmer attempts to use F2 generation seed, he will see a dramatic reduction in the amount of product produced by the F2 generation plants.

The use of a transcriptional protein also has the added advantage that several transgenes can be controlled by the same transactivating protein, without the problems of cosuppression seen with conventional cis acting systems.

By physically separating the promoter regulatory and target sequences within independent transgenic plants, different transgene expression can be selected for in the F1 generation simply by crossing the transgenic target line with regulator lines that express the transactivating protein in particular spatial and temporal patterns (eg. seed or leaf). Hence, this system allows the rapid introduction and fine-tuning of commercially attractive single or multiple gene traits in transgenic crops.

It also allows a useful tissue specific, but weakly expressed promoter to be used, since the transactivating protein works in low concentrations.

The preferred transactivating protein used is GAL4 from the yeast, *Saccharomyces cerevisiae*.

The expression of genes encoding enzymes of the galactose and melibiose metabolic pathways in the yeast *Saccharomyces cerevisiae* is stringently regulated by the available carbon source (Johnston, Microbiol. Rev., Vol. 51, pages 458–476 (1987)). Transcriptional control is mediated through the positive regulatory protein GAL4 and the negative regulatory protein GAL80. In the presence of galactose GAL4 divergently promotes transcription of the genes of the galactose regulon. Transcriptional activation by GAL4 results in a 1,000 fold increase in the level of gene expression. When the inducer is absent GAL80 inhibits the transactivating ability of GAL4. A number of additional transcriptional control mechanisms operate in the presence of glucose. These mechanisms, collectively termed catabolite repression, ensure that glucose is the preferred carbon source.

Native GAL4 is 881 amino acid (aa) residues in length and has a molecular weight of 99,000. Deletion and domain swap analyses have demonstrated that GAL4 is comprised of a number of functionally delineated domains, the combined activities of which account for the protein's in vivo characteristics (Ma & Ptashne, Cell. Vol. 48, pages 847–853, (1987); Brent & Ptashne, Cell. Vol. 43, pages 729–736, (1985). GAL4 binds to a 17 base-pair (bp) sequence exhibiting dyad symmetry, termed the galactose upstream activating sequence ($UA_{SG}$). In the presence of galactose GAL4 activates expression of genes linked to the $UA_{SG}$ (West et al., Mol.Cell.Biol., Vol. 4, pages 2467–2478) (1984). A consensus sequence of the naturally occurring site will also mediate GAL4 stimulatory action (Giniger et al., Cell, Vol. 40, pages 767–774, (1985); Lord et al., J. Mol. Biol., Vol. 186, pages 821–824 (1985). The amino terminal (N-terminal) 65aa residues of GAL4 are responsible for sequence specific-binding (Keegan et al., Sci. Vol. 231, pages 699–704 (1986); Johnston, Nature, Vol. 328, pages 353–355 (1987). Sequence-specific binding is absolutely dependent on the presence of a divalent cation coordinated by the 6 cysteine residues present in the DNA binding domain. The zinc-containing domain recognises a conserved CCG triplet at the end of each 17 bp site via direct contacts with the major groove (Marmorstein et al., Nature. Vol. 356, pages 408–414 (1992). Each target DNA sequence binds GAL4 as a dimer (Carey et al., J.Mol. Biol. Vol. 209, pages 423–432 (1989), a function ascribed to aa residues 65–94. Also present in the N-terminal 1–78aa residues is a nuclear localisation sequence (Silver et al, PNAS (USA), Vol. 81, pages 5951–5955 (1984).

Binding of GAL4 to its target DNA sequence is insufficient to direct RNA polymerase II dependent transcription of linked genes. The DNA binding function of the protein serves solely to position the carboxy-terminal (C-terminal) transcriptional activating domains in the vicinity of the promoter. Transcriptional activation is conferred by 2 major activating domains termed activating region I (ARI-aa residues 148–196) and activating region II (ARII-aa residues 767–881), of which ARII is the more potent (Ma & Ptashne, Supra). A third cryptic transactivating region (aa residues 75–147) has been identified in GAL4 deletion derivatives and exhibits in vitro activity (Lin et al., Cell. Vol. 54, pages 659–664 (1988). Each of the three transcriptional activation domains is characterised by a high proportion of negatively charged aa residues and hence are known as acidic activation domains (AAD). In the absence of a DNA-binding domain the activating regions are unable to function.

The mechanisms responsible for eukaryotic transcriptional activation have been evolutionary conserved. This is indicated by the fact that the yeast transcriptional activator GAL4 can activate gene expression in other eukaryotic organisms. Native GAL4 has been demonstrated to activate transcription of genes linked to the GAL4 binding site (either synthetic or the $UA_{SG}$) in insect (Fischer et al. (1987) and mammalian cells (Kakidani & Ptashne, Cell. Vol. 52, pages 161–167 (1988); Webster et al., Cell. Vol. 52, pages 169–178 (1988). Full length GAL4 is, however, incapable of stimulating transcription in plant protoplasts possibly as a result of its inefficient synthesis or instability (Ma et al., Nature, Vol. 334, pages 631–633 (1988). Deletion derivatives of GAL4 are able to activate transcription in yeast. These proteins, comprised of aa residues 1–147 (DNA-binding domain) and ARI and/or ARII also exhibit activity in mammalian cells (Kakidani & Ptashne, Supra) and plant protoplasts (Ma et al., Supra).

Two recent reports have demonstrated transgene expression of a target gene arranged in trans with a control gene in Drosophila (Brand & Perrimon, Development, Vol. 118, pages 401–415 (1993) and Crieg & Akam Nature, Vol. 362, pages 630–632 (1993)). Neither of these discuss the possibility of using such a system in plants.

The system described herein can be used to control the production of products or of a desired trait such as herbicide resistance. A preferred multigene system is the use of genes involved in the biosynthesis of polyhydroxybutyrate (PHB), controlled by a transactivating protein.

PHB is a commercially important biodegradable polymer which has previously been produced in plants using conventional cis acting control, as described in WO92/19747 (ICI) and Pimer et al (Science, Vol 256, pages 529–523 (1992)). It is, however, an ideal product to be produced by the invention since the multigene pathway is subject to the problems of cosuppression when used in conventional systems and the trans regulating system described herein enables the PHB to be produced more safely than existing methods of producing its implants.

It is therefore an object of the invention to produce an inherently safe method of producing a phenotypic trait in transgenic plants.

It is another object to produce a method of regulating two or more genes in a plant without the problems of cosuppression of the genes associated with conventional methods.

DESCRIPTION OF THE PREFERRED EMBODIMENTS

Figure 1A:
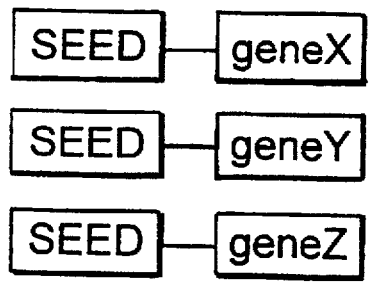
FIG. 1a is a diagrammatic representation of the conventional method of regulating gene expression using cis acting control elements.

A first aspect of the invention provides a method of producing a plant exhibiting one or more desired phenotypic traits, said method comprising the steps of:

fertilising a first transgenic plant with genetic material from a second transgenic plant to produce reproductive material, wherein:

one of the plants comprises at least one nucleic acid sequence encoding a desired phenotypic trait operatively linked to an upstream activating sequence (UAS) recognition site; and the other plant comprises nucleic acid encoding a promoter operatively linked to a nucleic acid sequence encoding a transactivating protein which is capable of activating said UAS sequence; and growing the reproductive material into a plant exhibiting the desired phenotypic trait.

A second aspect of the invention provides a method of producing plant reproductive material, said method comprising the steps of:

fertilising a first transgenic plant with genetic material from a second transgenic plant to produce the plant reproductive material, wherein:

one of the plants comprises at least one nucleic acid sequence encoding a desired phenotypic trait operatively linked to an upstream activating sequence (UAS) recognition site; and the other plant comprises nucleic acid encoding a promoter operatively linked to a nucleic acid sequence encoding a transactivating protein which is capable of activating said UAS sequence.

Preferably the first transgenic plant is pollinated from the second transgenic plant and the reproductive material may be seed.

Preferably the first transgenic plant is male sterile.

The phenotypic trait may for example be the production of a product or herbicide resistance.

In accordance with one embodiment a method for producing a plant exhibiting one or more desired phenotypic traits is described. The method comprises the steps of providing a first and second plant and pollinating the first plant with pollen from the second plant, wherein one of the plants comprises a nucleic acid sequence encoding for herbicide resistance, operatively linked to an upstream activating sequence that is activated by GAL4, and the other plant comprises a nucleic acid sequence encoding for GAL4, or a derivative thereof. Alternatively, one of the plants comprises a nucleic acid sequence encoding for the production of a polyhydroxyalkanoate operatively linked to an upstream activating sequence that is activated by GAL4, and the other plant comprises a nucleic acid sequence encoding for GAL4, or a derivative thereof.

A third aspect of the invention provides a method of controlling two or more genes in a plant comprising the steps of inserting into a plant;

two or more exogenous genes, each of which is operatively linked to a nucleic acid sequence encoding for a heterologous upstream activating sequence (UAS) recognition site; and nucleic acid encoding for a promoter operatively linked to a nucleic acid sequence encoding for a transactivating protein which is capable of activating the UAS sequence.

Preferably the transactivating protein used in the invention is GAL4 protein or a derivative thereof, preferably as encoded by or homologous with, the vector pGAL4. The UAS recognition site may be a site recognised by such proteins if they are used. A preferred UAS sequence is that used in plasmid pUMIGIT.

The plant used may be a plant in which transgenic DNA has been inserted, such as a soft fruit, tobacco, potato, barley, rice, legume, wheat, Brassica or Arabidopsis. The selection of the plant may be dependent on a number of factors such as the ease of growing the plant and the desired phenotypic trait.

In a preferred embodiment the phenotypic trait is the production of polyhydroxyalkanoates (PHA) such as polyhydroxybutyrate (PHB). The preferred genes controlled by UAS sequences are β-ketothiolase, NADP linked acetoacetyl CoA reductase and polyhydroxybutyrate synthase, as disclosed in WO92/19747.

PHB production requires large amounts of acetylcoenzyme A (acetyl CoA). Oil-producing plants such a Canola, Soya, Sunflower and most preferably Oilseed Rape (*Brassica napus*) may be used to produce PHB because oil production involves the production of large amounts of acetyl CoA.

The promoters used may be tissue specific to enable the desire phenotype to be specifically expressed, for example in seeds, leaves or roots.

Preferred promoters for use in the invention are CaMV35S constitutive promoter, the promoter of the rape seed storage protein, napin, cruciferin, and promoters for fatty acid synthesis such as rape acyl carrier protein (ACP) or β-ketoacyl ACP reductase. Plants and parts of plants produced directly by the methods of the invention or from the seeds or their progeny, including seed, are also included within the scope of the invention. The invention also provides products produced by the methods of the invention.

The gene constructs used in the invention may be produced and inserted into plants using conventional methods such as the use of Agrobacterium infection-methods or particle infiltration methods known in the art.

Bechtold et al (C. R. Acad. Sci., Paris Sciences de la view/Life Sciences, Vol. 316, pages 1194–9 (1993)), for example, discloses a vacuum infiltration method for infiltrating a suspension of Agrobacterium cells containing a binary T-DNA vector into Arabidopsis plants.

An alternative method, especially suitable for Brassica tissue transformation, uses young inflorescences which are sterilised and cut into segments. The segments are inverted and infected with *A. rhizogenes* containing T-DNA vectors with the transgenes of interest and cultured. The hairy roots produced are selected for transformants and multiplied in subculture. Root and leaves are induced to produce plants, and the plants are then backcrossed with wild type plants to allow gene segregation. The resulting progeny are then selected for a marker, such as NAM inhibition by NAA or Kanamycin resistance. The presence of a particular transgene can then be confirmed by PCR.

Figure 2:
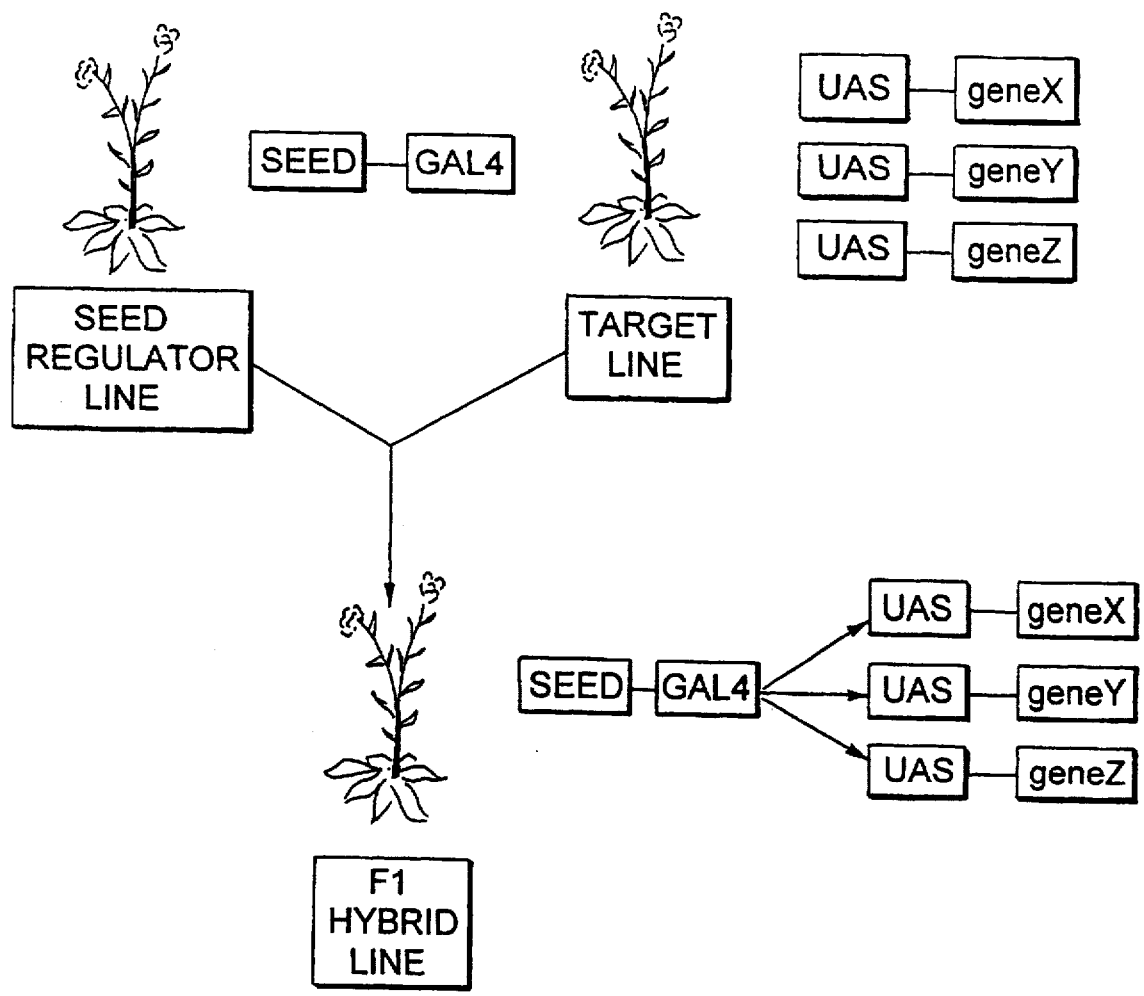
FIG. 2 is a schematic representation of the cross fertilization of a seed regulator plant line (which expresses the transactivating protein) with a target cell line (having multiple gene under the control of an upstream activating sequence, UAS) to produce an F1 hybrid that expresses the X, Y and Z gene products.
Figure 3A:
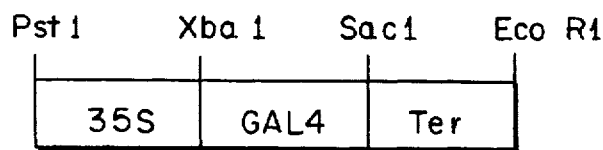
FIG. 3a is a schematic representation of one plasmid vector construct (pGAL4) suitable for use in the present invention.
Figure 3A:
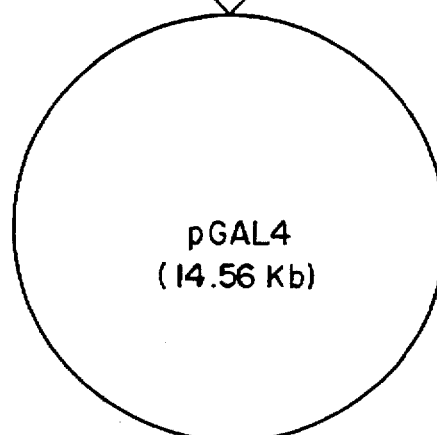

The invention will now be described with reference to the following Figures, in which:

FIG. 1 shows a) conventional methods of gene regulation, compared with b) the approach of the invention;

FIG. 2 demonstrates the segregation of regulatory and target sequences in plants;

FIG. 3a shows a schematic diagram of vector pGAL4, 3b) the GAL4 insert SEQ ID NO:1 represents the sequence of the GAL4 insert.

Figure 1B:
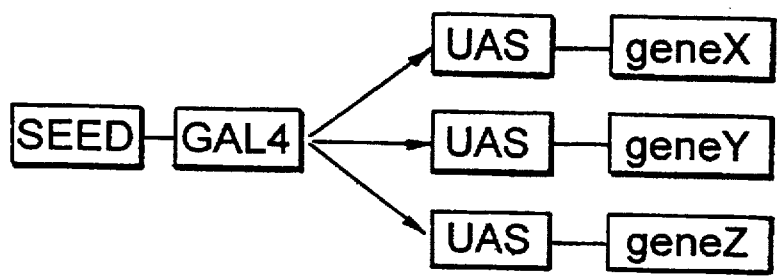
FIG. 1b is a diagrammatic representation of the regulatory mechanism utilized in the present invention, wherein the expression of multiple genes is regulated by a transactivating protein (i.e. GAL4).
Figure 4:
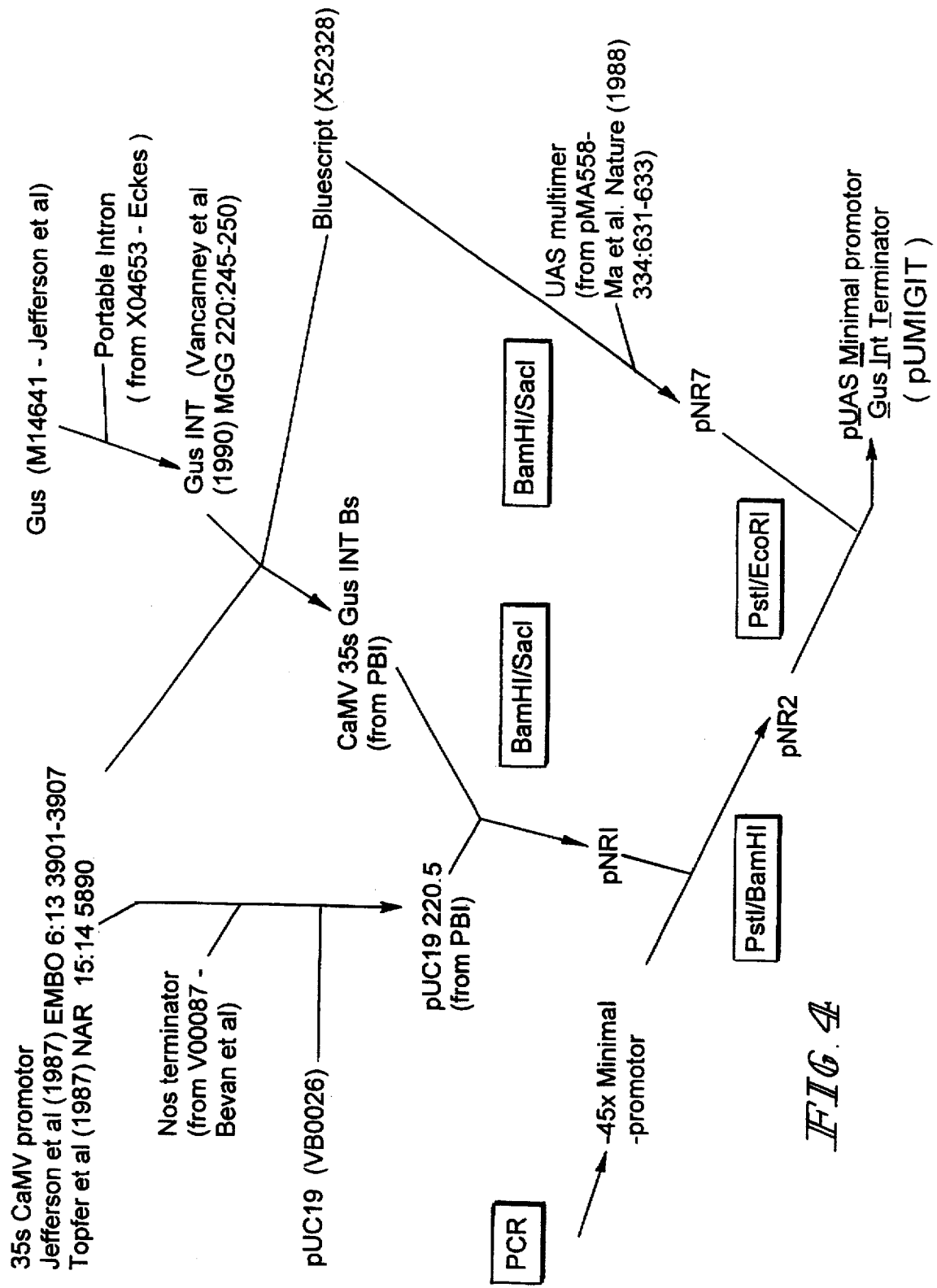
FIG. 4 is a diagrammatic representation of the strategy utilized to prepare the reporter plasmids used in the present invention.
Figure 5A:
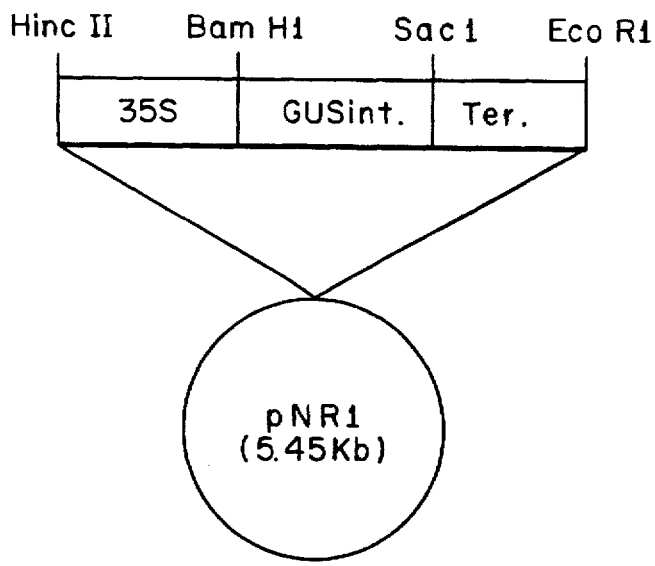
FIG. 5a is a schematic representation of plasmid construct pNR1.
Figure 5B:
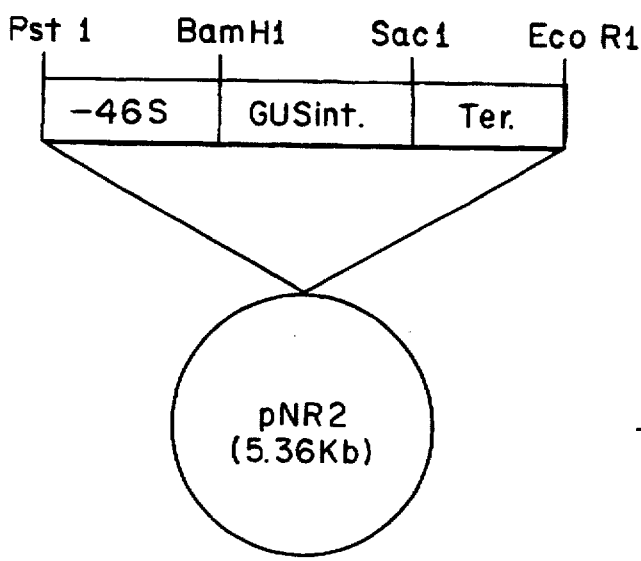
FIG. 5b is a schematic representation of plasmid construct pNR2.
Figure 5C:
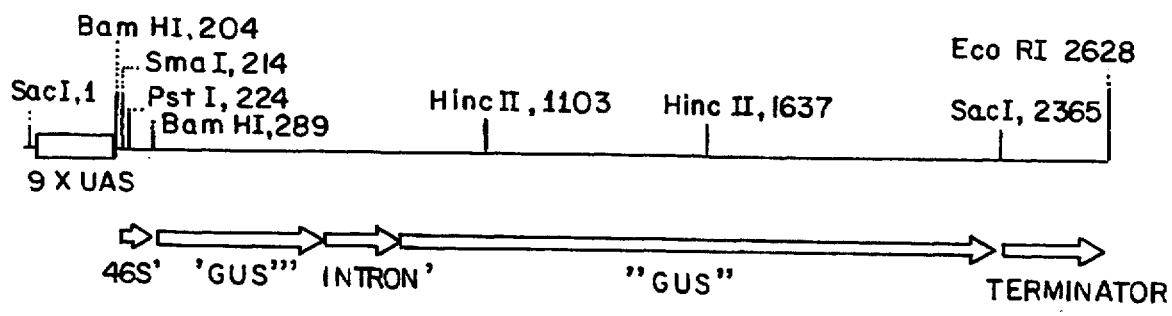
FIG. 5c is a schematic representation of the pUMIGIT insert which includes the reporter gene, GUSint, the 46S cauliflower mosaic virus promoter (CaMV) minimal promoter and the GAL4 binding sites (UAS).

FIG. 4 shows a flow diagram illustrating the production of reporter plasmids used; and FIGS. 5a through 5e illustrates the reporter plasmids used; FIG. 5a) shows pNR1, 5b) pNR2, 5c) the pUMIGIT insert, 5d) a schematic representation of pUMIGIT, and 5e) the plasmid pBI-221, wherein SEQ ID NO:2 represents the DNA sequence of the pUMIGIT insert sequence and SEQ ID NO:3 represents the complete sequence of the whole pUMIGIT plasmid FIG. 1a shows a conventional approach to controlling a multigene system in which each gene x, y and z is controlled by a separate seed promoter ("seed"). FIG. 1b shows the approach of the invention in which the seed promoter controls GAL4 transactivating protein production, which in turn activates a UAS sequence attached to each gene.

A major advantage of this is shown in FIG. 2 which shows a separate seed regulator plant line being crossed with a target cell line to produce regulated target genes in the F1 hybrids produced.

EXAMPLES

Tobacco Cells

In order to demonstrate the ability of GAL4 derivative to transactivate a transgene in plants, the following experiments were undertaken in tobacco cells:

Plasmid Constructions

All DNA constructions were performed using standard procedures as shown in Maniatis et al, (Molecular Cloning: A laboratory manual, 2nd edition, Cold Spring Harbour Laboratory Press (1989)).

Effector Plasmid pMA562, which contains a GAL4 derivative bearing GAL4 (1–147) and ARII was provided by Jun Ma and is disclosed in Ma et al, (Nature, vol. 334, pages 631–633 (1988)). For the construction of pGAL4 the 900 bp GAL4 (1–147)+ARII fragment was excised by partial digestion of pMA582 with Sau3A and inserted into the BamHI site of pUC19 (Yannisch-Perron et al, Gene, Vol. 33, pages 103–119 (1985)) creating pMB1. The 900 bpXbaI-SacI GAL4(1–147)+ARII fragment from pMBI was inserted into the XbaI-SacI cut binary vector pBI-121 (Jefferson et al, EMBO J, Vol. 6, pages 3901–3907, (1987)) downstream of the constitutively expressed 35S Cauliflower mosaic virus (CaMV) promoter (Odell et al, Nature, Vol. 313, pages 810–812) and upstream of the nopaline synthase (NOS) terminator of *Agrobacterium tumefaciens*, generating pGAL4.

Figure 3B:
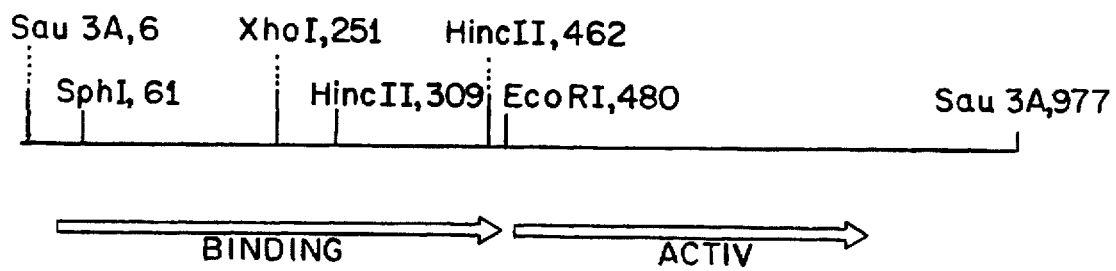
FIG. 3b is a schematic representation of the GAL4 insert, including the DNA binding site and region II activator sequences.

A schematic representation of pGAL 4 is shown in FIG. 3a. This illustrates the position of the CaMV35S promoter, GAL4) insert and NOS terminator in relation to restriction endonuclease sites. FIG. 3b) shows the GAL4 insert and the relationship of the DNA binding and region II activator sequences. The DNA sequence of the insert is represented by SEQ ID NO: 1.

Reporter plasmids

A summary of the production of the reporter plasmids used is shown in FIG. 4. The numbers in brackets are Genbank accession numbers, where these have not been available source journal references have been provided.

pUC19 220.5, which contains constitutively expressed 35SCaMV promoter and the NOS terminator, and CaMV35s GusINTBs, which contains the reporter gene β-glucuronidase, were provided by Robert Shields, PBI, Cambridge.

pNR1 was generated by excising the 2.1 Kb Bam H1-Sac1 GUSint fragment (Vanamneyt et al, Mol. Gen. Genet., Vol. 220, pages 245–250 (1990)) from CaMV35s Gus INT Bs, and inserting this into BamH1-Sac1 cut pUC19 220.5, as shown in FIG. 5a. This shows the relationship of the 35S promoter with the GUSint reporter gene and the termination sequence (Ter).

pNR2, a derivative of pNR1, contains the reporter gene GUSint under the control of the 46S CaMV minimal promoter. The 70bp-46S CaMV minimal promoter was obtained by PCR, using primers which delineate the 46S CaMV minimal promoter and contain Pst1 and BamH1 sites at their 5' and 3' ends respectively. The 70 bp fragment obtained was inserted into Pst1-BamH1 cut pNR1 (see FIG. 5b).

pUMIGIT, a derivative of pNR2 contains the reporter gene GUSint under the control of the 46S CaMV minimal promoter and 10 synthetic 17 bp GAL4 binding sites. The GAL4 binding sites were excised from pMA558 (provided by Jun Ma) as a 170 bp BamH1-Sac1 fragment and inserted into BamH1-Sac1 cut Bluescript (Trademark, Stratagene Ltd, Cambridge, UK) generating pNR7. The 2.4 Kb 46S GUSint-NOSter fragment was excised from pNR2 by Pst1-EcoR1 digestion and cloned into Pst1-EcoR1 cut pNR7 thereby generating pUMIGIT (see FIG. 5c).

Figure 5D:
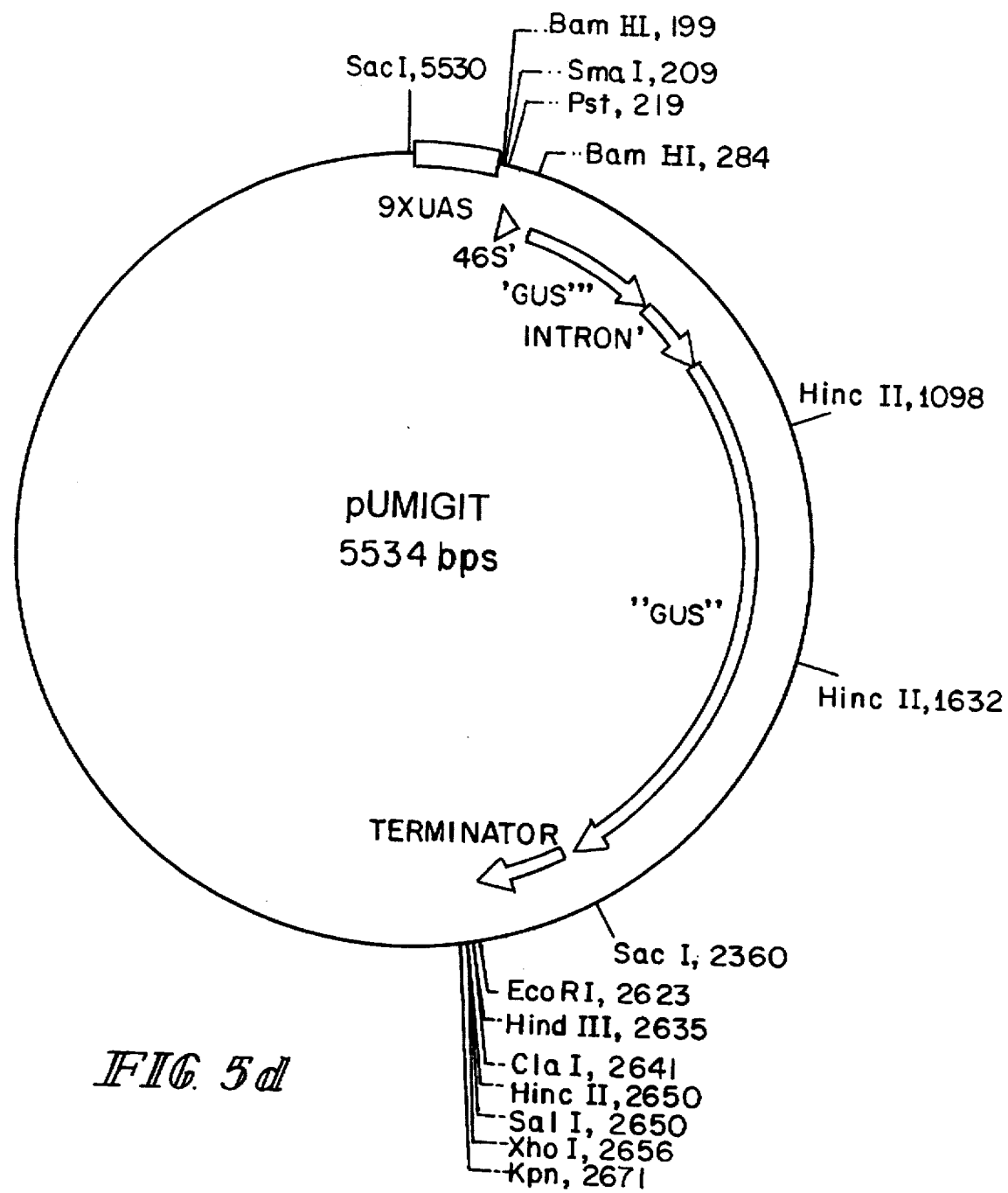
FIG. 5d is a schematic representation of plasmid construct pUMIGIT.
Figure 5E:
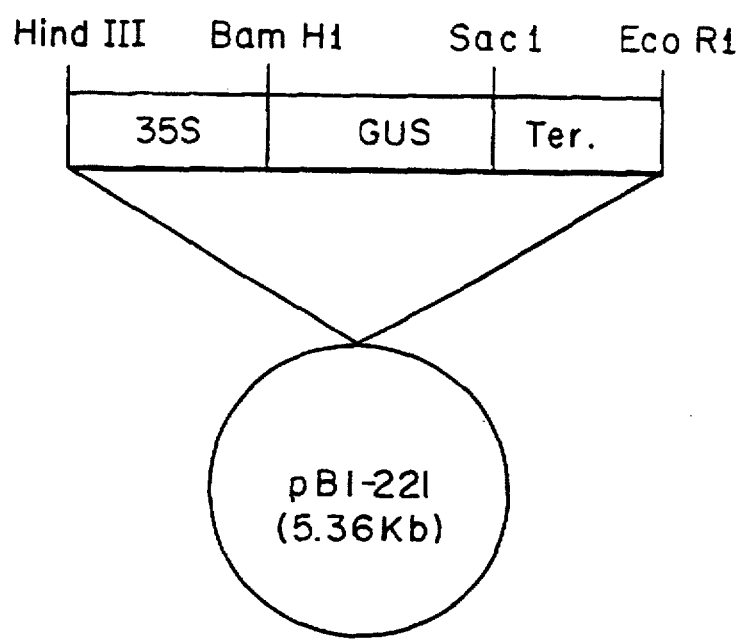
FIG. 5e is a schematic representation of plasmid construct pBI-221.

The sequence of the UAS-GUS construct in PUMIGIT is represented by SEQ ID NO:2, a schematic representation is shown in FIG. 5d and the complete sequence of pUMIGIT is represented by SEQ ID NO:3.

pBI-221 is comprised of CaMV35S promoter—GUS-NOS-ter pBI-121 (Jefferson et al, EMBO J; Vol. 6, pages 3701–3907 (1987)) cloned into pUC19 (Yannisch-Perron et al, supra) and was obtained from Robert Shields, PBI Cambridge. This is shown in FIG. 5e.

Large scale plasmid preparation

Large scale plasmid preparation was carried out on $CsCl_2$ gradients (Maniatis et al., Supra).

Plant Material

Tobacco suspension cells were obtained from Jean Evans, PBI Cambridge.

DNA/microprojectile preparation and bombardment conditions 60 mg of tungsten (1 μm diameter) particles were sterilised in 1 ml 96% ethanol for 5 minutes. During this period the suspension was vortexed. After washing with sterile water, particles were resuspended in 1 ml sterile water. 2.5 μg of each pNR1, pNR2 pNR8, pGAL4 and pBI-221 were precipitated onto the tungsten particles according to Sanford et al (Meth. Enzymol. Vol. 217, pages 483–509, (1993)). Particle bombardment of tobacco protoplasts was carried out using a helium-driven particle infiltration gun (PIG, Finer et al., Plant Cell Rep. Vol 11, pages 323–328, (1992)).

Histochemical Assay

Transient expression of the uida gene for β-glucuronidase (GUS) was visualised by staining in 1 mM 5-bromo-4-chloro-3-indolyl β-D-glucuronic acid (X-gluc Sigma, Poole, UK) as described by Jefferson et al., EMBO. J., Vol. 6, pages 3901–3907 (1987)).

Results and discussion

To initially demonstrate the GAL4 that can direct transcription of a UAS-linked reporter gene the following plasmids were introduced into tobacco cells using microprojectile bombardment:
a) pNR1 (35S-GUSint-NOSter) positive control
b) pNR2 (-46S-GUSint-NOSter) negative control
c) pUMIGIT (UAS-46S-GUSint-NOSter) reporter construct
d) pGAL4 (35S-GAL4-NOSter) effector construct.

A transient expression assay was utilised to achieve this aim, using microprojectile bombardment to introduce the test and control plasmids into tobacco suspension cells.

pBI-221, a plasmid construct known to express GUS in plant cells (Jefferson et al., Supra) acted as an internal positive control in these experiments. 48 h following particle bombardment the tobacco suspension cells were stained for GUS expression by calorimetric assay.

pNR1 also gave rise to transient GUS expression 48 h following particle bombardment. The level to which transient reporter gene expression was observed with pNR1 was only 40% of that observed using pBI-221 possibly as a result of inefficient intron processing. This result contrasts with the results of Vanamneyt et al, Mol. Gen. Genet. Vol. 220, page 445–250, (1990) who observed no difference between the levels of GUS activity from reporter plasmids bearing the β-glucuronidase gene with and without the intron in plant cells.

The -46S minimal CaMV promoter is unable to direct transcription of linked genes in plants due to the absence of upstream regulatory elements (Odell et al., Supra). Particle bombardment of tobacco cells with pNR2 did not, as would be expected, result in any detectable reporter gene expression.

In order to ascertain that no endogenous plant factor was capable of binding to the UAS and directing expression of the UAS-linked reporter gene, PUMIGIT, was transferred into tobacco suspension cells in the absence of the GAL4 regulator plasmid. No GUS activity could be detected in cells containing this construct alone.

When tobacco protoplasts were bombarded with pUMIGIT and pGAL4 GUS staining was observed. Enzyme activity could not be detected 48 hours following bombardment but, could be detected 7 days post-bombardment. The number of transfection events obtained (GUS-expressing cells identified as blue spots) was equivalent to the number obtained 48 h following bombardment with pNR1. The length of time required before enzyme activity could be detected under these circumstances probably reflects the requirement for two consecutive transcription and translation events to occur before the report gene is expressed.

To ensure that binding of GAL4 to the UAS is responsible for the observed reporter gene activity pGAL4, pNR2 and pGAL4 were transferred into tobacco suspension cells. No GUS staining could be detected in the suspension cells after 7 days of incubation with X-gluc.

These experiments illustrate that the constructs designed to develop the binary system in *Arabidopsis thaliana* and *Brassica napus* function in tobacco suspension cells.

Transactivation in Arabidopsis Plants

In a later experiment DNA comprising UAS-GUS-Ter linked to a hygromycin resistance gene and 35S-GAL4-Ter linked to a kanamycin resistance gene were each put in T-DNA vectors and co-transfected into Arabidopsis roots using Agrobacterium.

Co-transfected root cells were selected using hygromycin and kanamycin and grown into calli. Leaves produced from the calli were then stained for GUS production using X-gluc.

The stained veins of the leaf showed the successful transactivation of the UAS-GUS reporter gene by GAL4 in the Arabidopsis plant.

We claim:

1. A method of producing a plant exhibiting one or more desired phenotypic traits, wherein the improvement comprises the steps of:

(i) providing a first and a second transgenic plant;

(ii) pollinating the first transgenic plant with pollen from the second transgenic plant to produce an embryo or seed, wherein:

one of the transgenic plants comprises at least one nucleic acid sequence encoding for herbicide resistance or for the production of a polyhydroxyalkanoate, said nucleic acid sequence operatively linked to an upstream activating sequence recognition site; and the other transgenic plant comprises a nucleic acid sequence encoding for GAL4, or a derivative thereof which activates said upstream activating sequence; and (iii) growing the embryo or seed into a plant.

2. A method according to claim 1, wherein the first transgenic plant is male sterile.

3. A method according to claim 1, wherein the plant produced is selected from the group consisting of sunflower, canola, soybean and oilseed rape.

4. A plant produced by the method of claim 1, wherein the polyhydroxyalkanoate is polyhydroxybutyrate.

5. A method according to claim 1, wherein the plant produced is selected from the group consisting of blackberry, apple, pear, plum, cherry, raspberry, strawberry, damson, tobacco, potato, barley, rice, wheat, pea and bean.

6. A method according to claim 1, wherein the plant produced is selected from the group consisting of legumes, Brassica, and Arabidopsis.

7. A method according to claim 1, wherein the upstream activating sequence is the sequence within plasmid pUMIGIT.

8. A method of producing plant reproductive material, wherein the improvement comprises the steps of:

(i) providing a first and a second transgenic plant and;

(ii) pollinating the first transgenic plant with pollen from the second transgenic plant to produce an embryo or seed, wherein:

one of the transgenic plants comprises at least one nucleic acid sequence encoding for herbicide resistance or for the production of a polyhydroxyalkanoate, said nucleic acid sequence operatively linked to an upstream activating sequence recognition site; and the other transgenic plant comprises a nucleic acid sequence encoding for GAL4, or a derivative thereof which activates said upstream activating sequence.

9. A method according to claim 8, wherein the first transgenic plant is male sterile.

10. A method according to claim 8, wherein the the transgenic plants are selected from the group consisting of sunflower, canola, soybean and oilseed rape.

11. The method of claim 8, wherein the polyhydroxyalkanoate is polyhydroxybutyrate.

12. A method according to claim 8, wherein the plant produced is selected from the group consisting of blackberry, apple, pear, plum, cherry, raspberry, strawberry, damson, tobacco, potato, barley, rice, wheat, pea and bean.

13. A method according to claim 8, wherein the plant produced is selected from the group consisting of legumes, Brassica, and Arabidopsis.

14. A method according to claim 8, wherein the upstream activating sequence is the sequence within plasmid pUMIGIT.

15. A method of controlling two or more genes in a plant, wherein the improvement comprises the steps of inserting into a plant:

(i) two or more exogenous genes, each of which is operatively linked to a nucleic acid sequence encoding for a heterologous upstream activating sequence recognition site; and (ii) a nucleic acid sequence encoding for GAL4, or a derivative thereof, which activates the upstream activating sequence.

16. A method according to claim 15, wherein the plant is selected from the group consisting of blackberry, apple, pear, plum, cherry, raspberry, strawberry, damson, tobacco, potato, barley, rice, wheat, pea and bean.

17. A method according to claim 15, wherein the exogenous genes encode for the production of a polyhydroxyalkanoate, such as polyhydroxybutyrate.

18. A method according to claim 15, wherein the plant produced is selected from the group consisting of legumes, Brassica, and Arabidopsis.

19. A method according to claim 15, wherein the upstream activating sequence is the sequence within plasmid pUMIGIT.

20. A method according to claim 15, wherein the plant is selected from sunflower, canola, soybean and oilseed rape.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 980 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Saccharomyces cerevisiae ( v i i ) IMMEDIATE SOURCE:
( B ) CLONE: pGAL4

( x i ) SEQUENCE DESCRIPTION: SEQ ID NO:1:

```
CCCGCGATCA GCTTGAAGCA AGCCTCCTGA AAGATGAAGC TACTGTCTTC TATCGAACAA        60
GCATGCGATA TTTGCCGACT TAAAAAGCTC AAGTGCTCCA AAGAAAAACC GAAGTGCGCC       120
AAGTGTCTGA AGAACAACTG GGAGTGTCGC TACTCTCCCA AAACCAAAAG GTCTCCGCTG       180
ACTAGGGCAC ATCTGACAGA AGTGGAATCA AGGCTAGAAA GACTGGAACA GCTATTTCTA       240
CTGATTTTTC CTCGAGAAGA CCTTGACATG ATTTGAAAA TGGATTCTTT ACAGGATATA        300
AAAGCATTGT TAACAGGATT ATTTGTACAA GATAATGTGA ATAAAGATGC CGTCACAGAT       360
AGATTGGCTT CAGTGGAGAC TGATATGCCT CTAACATTGA GACAGCATAG AATAAGTGCT       420
ACATCATCAT CGGAAGAGAG TAGTAACAAA GGTCAAAGAC AGTTGACTGT ATCGTTCCGG       480
AATTCCGCCA ATTTTAATCA AAGTGGGAAT ATTGCTGATA GCTCATTGTC CTTCACTTTC       540
ACTAACAGTA GCAACGGTCC GAACCTCATA ACAACTCAAA CAAATTCTCA AGCGCTTTCA       600
CAACCAATTG CCTCCTCTAA CGTTCATGAT AACTTCATGA ATAATGAAAT CACGGCTAGT       660
AAAATTGATG ATGGTAATAA TTCAAAACCA CTGTCACCTG GTTGGACGGA CCAAACTGCG       720
TATAACGCGT TTGGAATCAC TACAGGGATG TTTAATACCA CTACAATGGA TGATGTATAT       780
AACTATCTAT TCGATGATGA AGATACCCCA CCAAACCCAA AAAAAGAGTA AAATGAATCG       840
TAGATACTGA AAAACCCCGC AAGTTCACTT CAACTGTGCA TCGTGCACCA TCTCAATTTC       900
TTTCATTTAT ACATCGTTTT GCCTTCTTTT ATGTAACTAT ACTCCTCTAA GTTTCAATCT       960
TGGCCATGTA ACCTCTGATC                                                  980
```

(2) INFORMATION FOR SEQ ID NO:2:

(i) SEQUENCE CHARACTERISTICS:
        (A) LENGTH: 2633 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: pUMIGIT(insert)

(xi) SEQUENCE DESCRIPTION: SEQ ID NO:2:

```
GAGCTCNNNN CCCGGAGGAC AGTACTCCGC CCCCGGAGGA CAGTACTCCG CCCCCGGAGG    60
ACAGTACTCC GCCCCCGGAG GACAGTACTC CGCCCCCGGA GGACAGTACT CCGCCCCCGG   120
AGGACAGTAC TCCGCCCCCG GAGGACAGTA CTCCGCCCCC GGAGGACAGT ACTCCGCCCC   180
CGGAGGACAG TACTCCGCCN NNNGGATCCN NNNCCCGGGN NNNCTGCAGA CTATCCTTCG   240
CAAGACCCTT CCTCTATATA AGGAAGTTCA TTTCATTYGG AGAGAACAGG ATCCNNNNGG   300
TCAGTCCCTT ATGTTACGTC CTGTAGAAAC CCCAACCCGT GAAATCAAAA AACTCGACGG   360
CCTGTGGGCA TTCAGTCTGG ATCGCGAAAA CTGTGGAATT GATCAGCGTT GGTGGGAAAG   420
CGCGTTACAA GAAAGCCGGG CAATTGCTGT GCCAGGCAGT TTTAACGATC AGTTCGCCGA   480
TGCAGATATT CGTAATTATG CGGGCAACGT CTGGTATCAG CGCGAAGTCT TTATACCGAA   540
AGGTTGGGCA GGCCAGCGTA TCGTGCTGCG TTTCGATGCG GTCACTCATT ACGGCAAAGT   600
GTGGGTCAAT AATCAGGAAG TGATGGAGCA TCAGGGCGGC TATACGCCAT TTGAAGCCGA   660
TGTCACGCCG TATGTTATTG CCGGGAAAAG TGTACGTAAG TTTCTGCTTC TACCTTTGAT   720
ATATATATAA TAATTATCAT TAATTAGTAG TAATATAATA TTTCAAATAT TTTTTTCAAA   780
ATAAAAGAAT GTAGTATATA GCAATTGCTT TTCTGTAGTT TATAAGTGTG TATATTTTAA   840
TTTATAACTT TTCTAATATA TGACCAAAAT TTGTTGATGT GCAGGTATCA CCGTTTGTGT   900
GAACAACGAA CTGAACTGGC AGACTATCCC GCCGGGAATG GTGATTACCG ACGAAAACGG   960
CAAGAAAAAG CAGTCTTACT TCCATGATTT CTTTAACTAT GCCGGAATCC ATCGCAGCGT  1020
AATGCTCTAC ACCACGCCGA ACACCTGGGT GGACGATATC ACCGTGGTGA CGCATGTCGC  1080
GCAAGACTGT AACCACGCGT CTGTTGACTG GCAGGTGGTG GCCAATGGTG ATGTCAGCGT  1140
TGAACTGCGT GATGCGGATC AACAGGTGGT TGCAACTGGA CAAGGCACTA GCGGGACTTT  1200
GCAAGTGGTG AATCCGCACC TCTGGCAACC GGGTGAAGGT TATCTCTATG AACTGTGCGT  1260
CACAGCCAAA GCCAGACAG AGTGTGATAT CTACCGCTT CGCGTCGGCA TCCGGTCAGT  1320
GGCAGTGAAG GGCCAACAGT TCCTGATTAA CCACAAACCG TTCTACTTTA CTGGCTTTGG  1380
TCGTCATGAA GATGCGGACT TACGTGGCAA AGGATTCGAT AACGTGCTGA TGGTGCACGA  1440
CCACGCATTA ATGGACTGGA TTGGGGCCAA CTCCTACCGT ACCTCGCATT ACCCTTACGC  1500
TGAAGAGATG CTCGACTGGG CAGATGAACA TGGCATCGTG GTGATTGATG AAACTGCTGC  1560
TGTCGGCTTT AACCTCTCTT TAGGCATTGG TTTCGAAGCG GGCAACAAGC CGAAAGAACT  1620
GTACAGCGAA GAGGCAGTCA ACGGGGAAAC TCAGCAAGCG CACTTACAGG CGATTAAAGA  1680
GCTGATAGCG CGTGACAAAA ACCACCCAAG CGTGGTGATG TGGAGTATTG CCAACGAACC  1740
GGATACCCGT CCGCAAGTGC ACGGGAATAT TCGCCACTG GCGGAAGCAA CGCGTAAACT  1800
```

-continued

```
CGACCCGACG CGTCCGATCA CCTGCGTCAA TGTAATGTTC TGCGACGCTC ACACCGATAC   1860
CATCAGCGAT CTCTTTGATG TGCTGTGCCT GAACCGTTAT TACGGATGGT ATGTCCAAAG   1920
CGGCGATTTG GAAACGGCAG AGAAGGTACT GGAAAAAGAA CTTCTGGCCT GGCAGGAGAA   1980
ACTGCATCAG CCGATTATCA TCACCGAATA CGGCGTGGAT ACGTTAGCCG GGCTGCACTC   2040
AATGTACACC GACATGTGGA GTGAAGAGTA TCAGTGTGCA TGGCTGGATA TGTATCACCG   2100
CGTCTTTGAT CGCGTCAGCG CCGTCGTCGG TGAACAGGTA TGGAATTTCG CCGATTTTGC   2160
GACCTCGCAA GGCATATTGC GCGTTGGCGG TAACAAGAAA GGGATCTTCA CTCGCGACCG   2220
CAAACCGAAG TCGGCGGCTT TTCTGCTGCA AAAACGCTGG ACTGGCATGA ACTTCGGTGA   2280
AAAACCGCAG CAGGGAGGCA ACAATGAAT CAACAACTCT CCTGGCGCAC CATCGTCGGC    2340
TACAGCCTCG GTGGGAATT NNNGAGCTC GATCGTTCAA ACATTGGCA ATAAAGTTTC      2400
TTAAGATTGA ATCCTGTTGC CGGTCTTGCG ATGATTATCA TATAATTTCT GTTGAATTAC   2460
GTTAAGCATG TAATAATTAA CATGTAATGC ATGACGTTAT TTATGAGATG GGTTTTTATG   2520
ATTAGAGTCC CGCAATTATA CATTTAATAC GCGATAGAAA ACAAAATATA GCGCGCAAAC   2580
TAGGATAAAT TATCGCGCGC GGTGTCATCT ATGTTACTAG ATCNNNGAA TTC           2633
```

( 2 ) INFORMATION FOR SEQ ID NO:3:

( i ) SEQUENCE CHARACTERISTICS:
      ( A ) LENGTH: 5534 base pairs
      ( B ) TYPE: nucleic acid
      ( C ) STRANDEDNESS: double
      ( D ) TOPOLOGY: circular ( i i ) MOLECULE TYPE: DNA (genomic)

( i i i ) HYPOTHETICAL: NO ( i v ) ANTI-SENSE: NO ( v i i ) IMMEDIATE SOURCE:
      ( B ) CLONE: pUMIGT ( x i ) SEQUENCE DESCRIPTION: SEQ ID NO:3:

```
CNNNNCCCGG AGGACAGTAC TCCGCCCCCG GAGGACAGTA CTCCGCCCCC GGAGGACAGT    60
ACTCCGCCCC CGGAGGACAG TACTCCGCCC CCGGAGGACA GTACTCCGCC CCCGGAGGAC   120
AGTACTCCGC CCCGGAGGA CAGTACTCCG CCCCGGAGG ACAGTACTCC GCCCCCGGAG    180
GACAGTACTC CGCCNNNNGG ATCCNNNNCC CGGGNNNNCT GCAGACTATC CTTCGCAAGA   240
CCCTTCCTCT ATATAAGGAA GTTCATTTCA TTYGAGAGA ACAGGATCCN NNNGGTCAGT    300
CCCTTATGTT ACGTCCTGTA GAAACCCCAA CCCGTGAAAT CAAAAAACTC GACGGCCTGT   360
GGGCATTCAG TCTGGATCGC GAAAACTGTG GAATTGATCA GCGTTGGTGG GAAAGCGCGT   420
TACAAGAAAG CCGGGCAATT GCTGTGCCAG GCAGTTTTAA CGATCAGTTC GCCGATGCAG   480
ATATTCGTAA TTATGCGGGC AACGTCTGGT ATCAGCGCGA AGTCTTTATA CCGAAAGGTT   540
GGGCAGGCCA GCGTATCGTG CTGCGTTTCG ATGCGGTCAC TCATTACGGC AAAGTGTGGG   600
TCAATAATCA GGAAGTGATG GAGCATCAGG GCGGCTATAC GCCATTTGAA GCCGATGTCA   660
CGCCGTATGT TATTGCCGGG AAAAGTGTAC GTAAGTTTCT GCTTCTACCT TTGATATATA   720
TATAATAATT ATCATTAATT AGTAGTAATA TAATATTTCA AATATTTTTT TCAAAATAAA   780
AGAATGTAGT ATATAGCAAT TGCTTTTCTG TAGTTTATAA GTGTGTATAT TTAATTTAT    840
AACTTTTCTA ATATATGACC AAAATTTGTT GATGTGCAGG TATCACCGTT TGTGTGAACA   900
ACGAACTGAA CTGGCAGACT ATCCCGCCGG GAATGGTGAT TACCGACGAA AACGGCAAGA   960
```

```
AAAAGCAGTC TTACTTCCAT GATTTCTTTA ACTATGCCGG AATCCATCGC AGCGTAATGC   1020
TCTACACCAC GCCGAACACC TGGGTGGACG ATATCACCGT GGTGACGCAT GTCGCGCAAG   1080
ACTGTAACCA CGCGTCTGTT GACTGGCAGG TGGTGGCCAA TGGTGATGTC AGCGTTGAAC   1140
TGCGTGATGC GGATCAACAG GTGGTTGCAA CTGGACAAGG CACTAGCGGG ACTTTGCAAG   1200
TGGTGAATCC GCACCTCTGG CAACCGGGTG AAGGTTATCT CTATGAACTG TGCGTCACAG   1260
CCAAAAGCCA GACAGAGTGT GATATCTACC CGCTTCGCGT CGGCATCCGG TCAGTGGCAG   1320
TGAAGGGCCA ACAGTTCCTG ATTAACCACA AACCGTTCTA CTTTACTGGC TTTGGTCGTC   1380
ATGAAGATGC GGACTTACGT GGCAAAGGAT TCGATAACGT GCTGATGGTG CACGACCACG   1440
CATTAATGGA CTGGATTGGG GCCAACTCCT ACCGTACCTC GCATTACCCT TACGCTGAAG   1500
AGATGCTCGA CTGGGCAGAT GAACATGGCA TCGTGGTGAT TGATGAAACT GCTGCTGTCG   1560
GCTTTAACCT CTCTTTAGGC ATTGGTTTCG AAGCGGGCAA CAAGCCGAAA GAACTGTACA   1620
GCGAAGAGGC AGTCAACGGG GAAACTCAGC AAGCGCACTT ACAGGCGATT AAAGAGCTGA   1680
TAGCGCGTGA CAAAAACCAC CCAAGCGTGG TGATGTGGAG TATTGCCAAC GAACCGGATA   1740
CCCGTCCGCA AGTGCACGGG AATATTTCGC CACTGGCGGA AGCAACGCGT AAACTCGACC   1800
CGACGCGTCC GATCACCTGC GTCAATGTAA TGTTCTGCGA CGCTCACACC GATACCATCA   1860
GCGATCTCTT TGATGTGCTG TGCCTGAACC GTTATTACGG ATGGTATGTC CAAAGCGGCG   1920
ATTTGGAAAC GGCAGAGAAG GTACTGGAAA AAGAACTTCT GGCCTGGCAG GAGAAACTGC   1980
ATCAGCCGAT TATCATCACC GAATACGGCG TGGATACGTT AGCCGGGCTG CACTCAATGT   2040
ACACCGACAT GTGGAGTGAA GAGTATCAGT GTGCATGGCT GGATATGTAT CACCGCGTCT   2100
TTGATCGCGT CAGCGCCGTC GTCGGTGAAC AGGTATGGAA TTTCGCCGAT TTTGCGACCT   2160
CGCAAGGCAT ATTGCGCGTT GGCGGTAACA AGAAAGGGAT CTTCACTCGC GACCGCAAAC   2220
CGAAGTCGGC GGCTTTTCTG CTGCAAAAAC GCTGGACTGG CATGAACTTC GGTGAAAAAC   2280
CGCAGCAGGG AGGCAAACAA TGAATCAACA ACTCTCCTGG CGCACCATCG TCGGCTACAG   2340
CCTCGGTGGG GAATTNNNNG AGCTCGATCG TTCAAACATT TGGCAATAAA GTTTCTTAAG   2400
ATTGAATCCT GTTGCCGGTC TTGCGATGAT TATCATATAA TTTCTGTTGA ATTACGTTAA   2460
GCATGTAATA ATTAACATGT AATGCATGAC GTTATTTATG AGATGGGTTT TTATGATTAG   2520
AGTCCCGCAA TTATACATTT AATACGCGAT AGAAAACAAA ATATAGCGCG CAAACTAGGA   2580
TAAATTATCG CGCGCGGTGT CATCTATGTT ACTAGATCNN NNGAATTCGA TATCAAGCTT   2640
ATCGATACCG TCGACCTCGA GGGGGGGCCC GGTACCCAAT TCGCCCTATA GTGAGTCGTA   2700
TTACGCGCGC TCACTGGCCG TCGTTTTACA ACGTCGTGAC TGGGAAAACC CTGGCGTTAC   2760
CCAACTTAAT CGCCTTGCAG CACATCCCCC TTTCGCCAGC TGGCGTAATA GCGAAGAGGC   2820
CCGCACCGAT CGCCCTTCCC AACAGTTGCG CAGCCTGAAT GGCGAATGGG ACGCGCCCTG   2880
TAGCGGCGCA TTAAGCGCGG CGGGTGTGGT GGTTACGCGC AGCGTGACCG CTACACTTGC   2940
CAGCGCCCTA GCGCCCGCTC CTTTCGCTTT CTTCCCTTCC TTTCTCGCCA CGTTCGCCGG   3000
CTTTCCCCGT CAAGCTCTAA ATCGGGGGCT CCCTTTAGGG TTCCGATTTA GTGCTTTACG   3060
GCACCTCGAC CCCAAAAAAC TTGATTAGGG TGATGGTTCA CGTAGTGGGC CATCGCCCTG   3120
ATAGACGGTT TTTCGCCCTT TGACGTTGGA GTCCACGTTC TTTAATAGTG GACTCTTGTT   3180
CCAAACTGGA ACAACACTCA ACCCTATCTC GGTCTATTCT TTTGATTTAT AAGGGATTTT   3240
GCCGATTTCG GCCTATTGGT TAAAAAATGA GCTGATTTAA CAAAATTTA ACGCGAATTT   3300
TAACAAAATA TTAACGCTTA CAATTTAGGT GGCACTTTTC GGGGAAATGT GCGCGGAACC   3360
```

```
CCTATTTGTT TATTTTTCTA AATACATTCA AATATGTATC CGCTCATGAG ACAATAACCC    3420
TGATAAATGC TTCAATAATA TTGAAAAAGG AAGAGTATGA GTATTCAACA TTTCCGTGTC    3480
GCCCTTATTC CCTTTTTTGC GGCATTTTGC CTTCCTGTTT TTGCTCACCC AGAAACGCTG    3540
GTGAAAGTAA AAGATGCTGA AGATCAGTTG GGTGCACGAG TGGGTTACAT CGAACTGGAT    3600
CTCAACAGCG GTAAGATCCT TGAGAGTTTT CGCCCCGAAG AACGTTTTCC AATGATGAGC    3660
ACTTTTAAAG TTCTGCTATG TGGCGCGGTA TTATCCCGTA TTGACGCCGG GCAAGAGCAA    3720
CTCGGTCGCC GCATACACTA TTCTCAGAAT GACTTGGTTG AGTACTCACC AGTCACAGAA    3780
AAGCATCTTA CGGATGGCAT GACAGTAAGA GAATTATGCA GTGCTGCCAT AACCATGAGT    3840
GATAACACTG CGGCCAACTT ACTTCTGACA ACGATCGGAG GACCGAAGGA GCTAACCGCT    3900
TTTTTGCACA ACATGGGGGA TCATGTAACT CGCCTTGATC GTTGGGAACC GGAGCTGAAT    3960
GAAGCCATAC CAAACGACGA GCGTGACACC ACGATGCCTG TAGCAATGGC AACAACGTTG    4020
CGCAAACTAT TAACTGGCGA ACTACTTACT CTAGCTTCCC GGCAACAATT AATAGACTGG    4080
ATGGAGGCGG ATAAAGTTGC AGGACCACTT CTGCGCTCGG CCCTTCCGGC TGGCTGGTTT    4140
ATTGCTGATA AATCTGGAGC CGGTGAGCGT GGGTCTCGCG GTATCATTGC AGCACTGGGG    4200
CCAGATGGTA AGCCCTCCCG TATCGTAGTT ATCTACACGA CGGGGAGTCA GGCAACTATG    4260
GATGAACGAA ATAGACAGAT CGCTGAGATA GGTGCCTCAC TGATTAAGCA TTGGTAACTG    4320
TCAGACCAAG TTTACTCATA TATACTTTAG ATTGATTTAA AACTTCATTT TTAATTTAAA    4380
AGGATCTAGG TGAAGATCCT TTTTGATAAT CTCATGACCA AAATCCCTTA ACGTGAGTTT    4440
TCGTTCCACT GAGCGTCAGA CCCCGTAGAA AAGATCAAAG GATCTTCTTG AGATCCTTTT    4500
TTTCTGCGCG TAATCTGCTG CTTGCAAACA AAAAAACCAC CGCTACCAGC GGTGGTTTGT    4560
TTGCCGGATC AAGAGCTACC AACTCTTTTT CCGAAGGTAA CTGGCTTCAG CAGAGCGCAG    4620
ATACCAAATA CTGTCCTTCT AGTGTAGCCG TAGTTAGGCC ACCACTTCAA GAACTCTGTA    4680
GCACCGCCTA CATACCTCGC TCTGCTAATC CTGTTACCAG TGGCTGCTGC CAGTGGCGAT    4740
AAGTCGTGTC TTACCGGGTT GGACTCAAGA CGATAGTTAC CGGATAAGGC GCAGCGGTCG    4800
GGCTGAACGG GGGGTTCGTG CACACAGCCC AGCTTGGAGC GAACGACCTA CACCGAACTG    4860
AGATACCTAC AGCGTGAGCT ATGAGAAAGC GCCACGCTTC CCGAAGGGAG AAAGGCGGAC    4920
AGGTATCCGG TAAGCGGCAG GGTCGGAACA GGAGAGCGCA CGAGGGAGCT TCCAGGGGGA    4980
AACGCCTGGT ATCTTTATAG TCCTGTCGGG TTTCGCCACC TCTGACTTGA GCGTCGATTT    5040
TTGTGATGCT CGTCAGGGGG GCGGAGCCTA TGGAAAAACG CCAGCAACGC GGCCTTTTTA    5100
CGGTTCCTGG CCTTTTGCTG GCCTTTTGCT CACATGTTCT TTCCTGCGTT ATCCCCTGAT    5160
TCTGTGGATA ACCGTATTAC CGCCTTTGAG TGAGCTGATA CCGCTCGCCG CAGCCGAACG    5220
ACCGAGCGCA GCGAGTCAGT GAGCGAGGAA GCGGAAGAGC GCCCAATACG CAAACCGCCT    5280
CTCCCCGCGC GTTGGCCGAT TCATTAATGC AGCTGGCACG ACAGGTTTCC CGACTGGAAA    5340
GCGGGCAGTG AGCGCAACGC AATTAATGTG AGTTAGCTCA CTCATTAGGC ACCCCAGGCT    5400
TTACACTTTA TGCTTCCGGC TCGTATGTTG TGTGGAATTG TGAGCGGATA ACAATTTCAC    5460
ACAGGAAACA GCTATGACCA TGATTACGCC AAGCGCGCAA TTAACCCTCA CTAAAGGGAA    5520
CAAAAGCTGG AGCT                                                     5534
```